United States Patent [19]
Bruns, Jr. et al.

[11] Patent Number: 5,514,675
[45] Date of Patent: May 7, 1996

[54] NAPHTHYL BRADYKININ RECEPTOR ANTAGONISTS

[75] Inventors: Robert F. Bruns, Jr., Carmel; Donald R. Gehlert, Indianapolis, both of Ind.; J. Jeffry Howbert, Bellevue, Wash.; William H. W. Lunn, Indianapolis, Ind.

[73] Assignee: Eli Lilly and Company, Indianapolis, Ind.

[21] Appl. No.: 327,519

[22] Filed: Oct. 20, 1994

[51] Int. Cl.$^6$ .................... C07C 49/203; C07C 49/115; C07C 49/00

[52] U.S. Cl. .............. 514/229.5; 514/248; 514/280; 514/284; 514/393; 514/400; 514/724; 568/303; 568/305; 568/308; 568/326

[58] Field of Search ............. 514/229.5, 248, 514/280, 284, 393, 400, 724; 568/303, 305, 308, 326

[56] References Cited

U.S. PATENT DOCUMENTS

| | | | |
|---|---|---|---|
| 4,230,862 | 10/1980 | Suarez et al. | 546/237 |
| 5,028,613 | 7/1991 | Sun et al. | 514/292 |
| 5,059,624 | 10/1991 | Monache et al. | 514/616 |
| 5,166,161 | 11/1992 | Kokura et al. | 514/314 |
| 5,212,165 | 5/1993 | Aberg et al. | 514/114 |
| 5,212,182 | 5/1993 | Musser et al. | 514/314 |
| 5,228,725 | 2/1994 | Witherup et al. | 514/292 |
| 5,288,725 | 2/1994 | Witherup et al. . | |

*Primary Examiner*—Jeffrey Mullis
*Attorney, Agent, or Firm*—Paul J. Gaylo; David E. Boone

[57] ABSTRACT

This invention provides methods of treating a physiological disorder associated with an excess of bradykinins in a mammal which comprises administering to a mammal in need of said treatment a compound selected from a series of substituted dihydronaphthalenes and naphthalenes.

18 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:

```
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Arg  Pro  Pro  Gly  Phe  Ser  Pro  Phe  Arg
    1                   5

(2) INFORMATION FOR SEQ ID NO:2:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Lys  Arg  Pro  Pro  Gly  Phe  Ser  Pro  Phe  Arg
    1                   5                        10

(2) INFORMATION FOR SEQ ID NO:3:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Met  Lys  Arg  Pro  Pro  Gly  Phe  Ser  Pro  Phe  Arg
    1                        5                        10
```

NAPHTHYL BRADYKININ RECEPTOR ANTAGONISTS

BACKGROUND OF THE INVENTION

Bradykinin is a nonapeptide having the amino acid sequence

Arg-Pro-Pro-Gly-Phe-Ser-Pro-Phe-Arg hereinafter referred to as SEQ ID NO:1, belonging to a family of kinins that also includes kallidin or lysyl-bradykinin which has the amino acid sequence Lys-Arg-Pro-Pro-Gly-Phe-Ser-Pro-Phe-Arg hereinafter referred to as SEQ ID NO:2, and methionyl-lysyl-bradykinin, which has the amino acid sequence Met-Lys-Arg-Pro-Pro-Gly-Phe-Ser-Pro-Phe-Arg hereinafter referred to as SEQ ID NO:3. These kinins are released from plasma precursors (kininogens) by the action of plasma and tissue kallikreins to regulate the essential physiological functions. [For a review of the therapeutic prospects of bradykinin receptor antagonists, see, J. N. Sharma, *General Pharmacology* 24:267–274 (1993).]

Bradykinin mediates pain, vascular permeability, inflammation, gastrointestinal function, and smooth muscle tone in vascular and other tissues. Bradykinin is one of the key mediators of the body's response to trauma and injury. Abnormally raised bradykinin release in response to noxious agents, tissue injury or lack of circulating kininases can induce several pathological conditions ranging from rheumatoid arthritis to asthma.

Receptors for bradykinin exist in the nervous system, epithelia, smooth muscle, and fibroblasts. In each tissue type bradykinin triggers specific responses including neurotransmitter release, muscle contraction, fluid secretion by epithelia, and stimulation of cell growth. The initial interaction for the biological response occurs at a bradykinin receptor site on a cell.

Bradykinin can activate neurons and produce neurotransmitter release. It can activate phospholipases C and $A_2$ resulting in the production of a number of bioactive intermediates.

Bradykinin receptors are G protein-coupled receptors that activate phospholipase C or phospholipase $A_2$ and increase the synthesis of inositol triphosphate, diacylglycerol, and arachidonic acid. Olsen, et al., *Journal of Bioloical Chemistry*, 263:18030–18035 (1988). G proteins are a family of membrane proteins that become activated only after binding guanosine triphosphate. Activated G proteins in turn activate an amplifier enzyme on the inner face of a membrane; the enzyme then converts precursor molecules into second messengers.

Bradykinin receptors have been classified as $B_1$ and $B_2$ on the basis of the relative potencies of agonists (kinins) and antagonists (kinin analogues) on various pharmacological preparations. R. J. Vavrek and J. M. Stewart, *Peptides*, 6:161–164 (1985). $B_1$ receptors are generated de novo in the vascular smooth muscle during incubation of isolated tissue and during antigen-induced arthritis. J. Bouthiller, et al., *British Journal of Pharmacology*, 92:257–264 (1987).

There continues to exist a need for non-peptidyl bradykinin receptor antagonists. Pharmacological agents containing guanidine moieties are known. See, e.g., U.S. Pat. Nos. 5,059,624 and 5,028,613. These two issued patents describe a series of pyrroloquinoline alkaloids isolated and purified from certain marine sponges. U.S. Pat. No. 5,288,725, issued Feb. 22, 1994, describes a series of pyrroloquinoline guanidine compounds useful as bradykinin receptor antagonists. U.S. Pat. No. 5,212,182, issued May 18, 1993, describes a series of quinolinyl- and naphthalenylbenzamides and benzylamines which are useful as bradykinin receptor antagonists possessing analgesic properties. U.S. Pat. No. 5,216,165, issued Jun. 1, 1993, describes a series of N-substituted aminoquinolines useful as analgesic agents by means of their properties as bradykinin receptor antagonists.

There continues to exist a need for efficacious and safe compounds which are useful as bradykinin receptor antagonists. The current invention provides a novel series of such antagonists which are administrable by a variety of routes, including orally as well as parenterally.

SUMMARY OF THE INVENTION

This invention provides a method of treating or preventing a physiological disorder associated with an excess of bradykinin in a mammal which comprises administering to a mammal in need thereof a therapeutically effective amount of a compound of Formula I

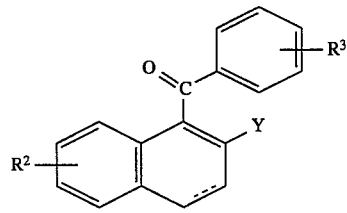

wherein:
$R^2$ is hydrogen, hydroxy, or $C_1$–$C_6$ alkoxy;
the dotted line represents an optional covalent bond;
Y is hydroxy, or

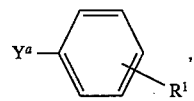

where
$Y^a$ is a bond, —$CH_2$—, or —$CH_2CH_2$—; and
$R^1$ is hydrogen, $C_1$–$C_6$ alkyl, $C_1$–$C_6$ alkoxy, or hydroxy;
$R^3$ is aryloxy, $C_1$–$C_6$ alkoxy, hydroxy or -Q-(CH$_2$)$_n$—NR$^a$R$^b$ where,
Q is —O— or —$CH_2$—,
n is 1–6,
$R^a$ and $R^b$ are independently hydrogen or $C_1$–$C_6$ alkyl or are taken together with the nitrogen to which they are bonded to constitute a heterocyclic ring selected from the group consisting of pyrrolidinyl, piperazinyl, 4-methylpiperidinyl, piperidinyl, hexamethyleneiminyl, imidazolinyl, heptamethyleneiminyl, morpholinyl, and N-methylpyrrolidinyl;
or a pharmaceutically acceptable salt, solvate, or prodrug thereof.

DETAILED DESCRIPTION AND PREFERRED EMBODIMENTS

The terms and abbreviations used in the instant examples have their normal meanings unless otherwise designated.

For example "°C." refers to degrees Celsius; "N" refers to normal or normality; "mmol" refers to millimole or millimoles; "g" refers to gram or grams; "ml" means milliliter or milliliters; "M" refers to molar or molarity; "MS" refers to mass spectrometry; "IR" refers to infrared spectroscopy; and "NMR" refers to nuclear magnetic resonance spectroscopy.

As used herein, the term "$C_1$–$C_6$ alkyl" refers to a straight or branched, monovalent, saturated aliphatic chain of 1 to 6 carbon atoms and includes, but is not limited to, methyl, ethyl, propyl, isopropyl, butyl, isobutyl, t-butyl, pentyl, isopentyl, and hexyl. Similarly, the term "$C_4$–$C_7$ alkyl" refers to a straight or branched, monovalent, saturated aliphatic chain of 4 to 7 carbon atoms.

"Halo" represents chloro, fluoro, bromo or iodo.

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like.

The term "di($C_1$–$C_6$ alkyl)amino" refers to a compound of the formula —$NR^xR^y$ wherein $R^x$ and $R^y$ are independently a $C_1$–$C_6$ alkyl group. Typical di($C_1$–$C_6$ alkyl)amino groups include dimethylamino, methylethylamino, diisopropylamino, ethylisopropylamino, and the like.

The term "leaving group" as used herein refers to a group of atoms that is displaced from a carbon atom by the attack of a nucleophile in a nucleophilic substitution reaction. The term "leaving group" as used in this document encompasses, but is not limited to, activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succinimidoxy, phthalimidoxy, benzotriazolyloxy, benzenesulfonyloxy, methanesulfonyloxy, toluenesulfonyloxy, azido, or —O—CO—($C_4$–$C_7$ alkyl).

Although the free-base form of those compounds of Formula I which have a basic functionality may be used in the methods of the present invention, it is preferred to prepare and use a pharmaceutically acceptable salt form. Thus, the compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention.

The term "pharmaceutically acceptable salt" as used herein, refers to salts of the compounds of the above formula which are substantially non-toxic to living organisms. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, pamoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of Formula I with an equimolar or excess amount of acid. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

It should be recognized that the particular counterion forming a part of any salt of this invention is usually not of a critical nature, so long as the salt as a whole is pharmacologically acceptable and as long as the counterion does not contribute undesired qualities to the salt as a whole.

This invention further encompasses the pharmaceutically acceptable solvates of the compounds of Formula I. Many of the Formula I compounds can combine with solvents such as water, methanol, ethanol and acetonitrile to form pharmaceutically acceptable solvates such as the corresponding hydrate, methanolate, ethanolate and acetonitrilate.

Many of the compounds employed in the present invention are derivatives of naphthalene which are named and numbered according to the RING INDEX, The American Chemical Society, as follows.

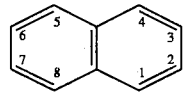

In a similar manner some of the compounds employed in the present invention are derivatives of 1,2-dihydronaphthalene which are named and numbered according to the RING INDEX as follows.

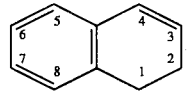

The compounds employed in the present invention may be prepared essentially as described in U.S. Pat. No. 4,230,862, issued to T. Suarez and C. D. Jones on Oct. 28, 1990, which is herein incorporated by reference.

In addition to being useful in the methods of the instant invention, those compounds employed in the methods of this invention in which $R^3$ is hydroxy are useful as intermediates in the preparation of other compounds of this invention. A preferred subclass of the compounds of this invention are the dihydronaphthalenes, having a basic side chain that is, in the above formula, those compounds in which $R^3$ is

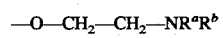

—O—$CH_2$—$CH_2$—$NR^aR^b$ in which —NR$^a$R$^b$ are a heterocyclic group or dimethylamino. Especially preferred methods of this invention employ those compounds wherein —NR$^a$R$^b$ is pyrrolidinyl, piperidinyl, piperazinyl, or dimethylamino.

The compounds of the present invention can be prepared by a variety of procedures well known to those of ordinary skill in the art. The particular order of steps required to produce the compounds of Formula I is dependent upon the particular compound being synthesized, the starting compound, and the relative lability of the substituted moieties.

The compounds employed in this invention are prepared by the following sequences, the dihydronaphthalene structures in general being precursors to the napththalene compounds.

A. Preparation of Dihydronapthalenyl Compounds

The compounds employed in the methods of the instant invention may be prepared by reacting a tetralone of Formula II

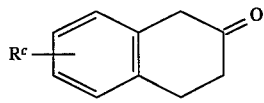

in which R$^c$ is hydrogen, C$_1$–C$_6$ alkoxy, or benzyloxy with a phenyl benzoate of Formula III

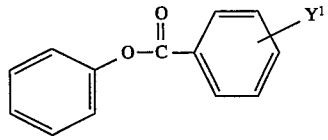

in which Y$^1$ is methoxy, benzyloxy, or —O—(CH$_2$)$_n$—NR$^a$R$^b$. This reaction is generally carried out in the presence of a moderately strong base such as sodium amide and at room temperature or below.

The product which is obtained is a substituted tetralone of Formula IV.

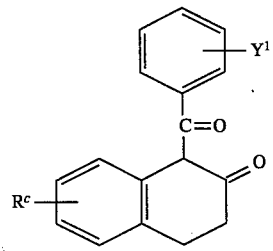

This substituted tetralone is then reacted under Grignard reaction conditions with the Grignard reagent of the formula

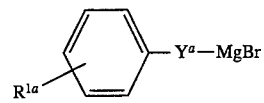

in which R$^{1a}$ is hydrogen, C$_1$–C$_6$ alkoxy, or benzyloxy.

The compounds which are produced, 3-phenyl-4-aroyl-1,2-dihydronaphthalenes, have the following formula, Formula V.

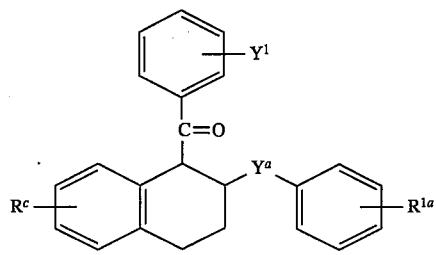

In those instances in which Y$^1$ is methoxy, a compound of Formula V can be treated with pyridine hydrochloride at reflux to produce the corresponding hydroxy compound. Under these conditions, should R$^c$ or R$^{1a}$ be alkoxy or benzyloxy, these groups will also be cleaved, resulting in hydroxy groups.

In those instances in which Y$^1$ is methoxy or benzyloxy, and R$^c$ or R$^{1a}$ is alkoxy or benzyloxy, the group at Y$^1$ can be selectively cleaved by treating a compound of Formula V with an equivalent of sodium thioethoxide in N,N-dimethylformamide at a moderately elevated temperature of about 80° C. to about 90° C. The process of the selective cleavage may be monitored by periodic thin layer chromatography analysis. The reaction is complete when little or no starting material remains.

Once the compound of Formula V in which Y$^1$ has been converted to hydroxy has been generated, that compound can then be treated with a compound of Formula VII

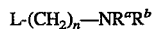

L-(CH$_2$)$_n$—NR$^a$R$^b$     VII wherein L is a good leaving group such as halo, especially chloro. Under the usual reaction conditions, of course, alkylation will be effected at each of the unprotected hydroxy groups which are present in the molecule. This can be avoided, and alkylation at the 4-benzoyl groups alone can be achieved, by carrying out the reaction in the presence of an excess of finely powdered potassium carbonate and using an equivalent or slight excess of the compound of Formula VII.

Depending upon the intended structure of the final product, the compound containing the substituent of Formula VII can then be further treated with an additional quantity of sodium thioethoxide in N,N-dimethylformamide as aforedescribed to effect cleavage of any remaining alkoxy or benzyloxy groups, thereby providing another sequence for achieving formation of those compounds employed in this invention in which R$^1$ and/or R$^2$ are hydroxy.

In any of the above, it is evident that the particular sequence of synthetic steps designed to produce a compound having substituents of particular definition and location is such as one of ordinary skill in the art will well recognize.

In another route for preparing the compounds of Formula I, compounds of Formula VI

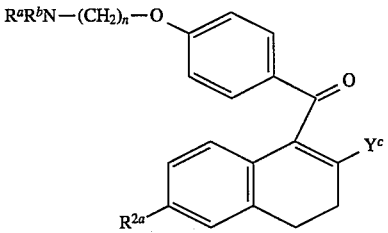

wherein: R$^{2a}$ is —H or C$_1$–C$_6$ alkoxy; and Y$^c$ is C$_1$–C$_6$ alkoxy-substituted phenyl or benzyl, are prepared essentially as described by C. D. Jones, et al., *Journal of Medicinal Chemistry*, 53:931–938 (1992), which is herein incorporated by reference.

Generally, a tetralone, as described above, or a salt thereof, is acylated using standard Friedel Crafts conditions to provide a highly enolized diketone of formula VIa

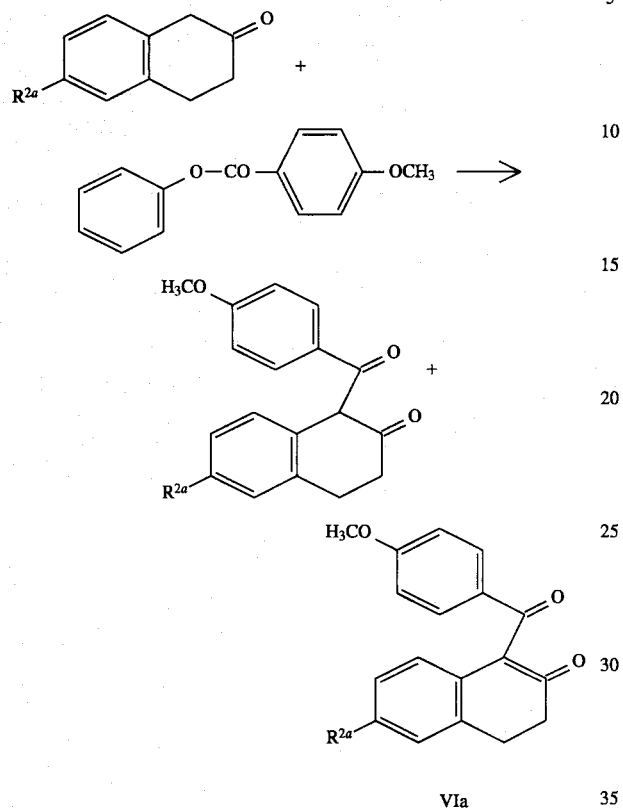

VIa wherein $R^{2a}$ is —H or $C_1$–$C_6$ alkoxy.

Subsequent derivatization using sodium hydride, followed by the addition of diphenyl chlorophosphate, gives the enol phosphate derivative tentatively assigned the Formula VIb

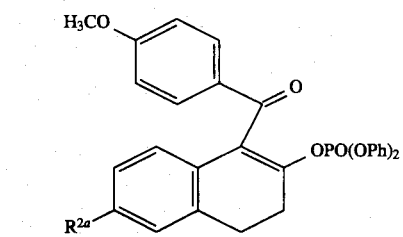

VIb wherein $R^{2a}$ is as defined above.

Addition of phenyl- or benzyl-, substituted phenyl- or substituted benzylmagnesium bromide to a compound of formula VIb, and subsequent selective demethylation provide compounds of formula VIc and VId, respectively, as described by Jones, supra.

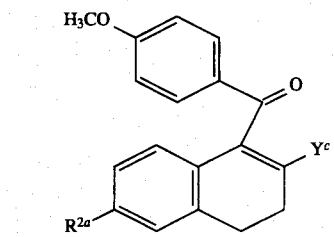

VIc

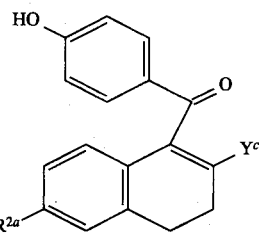

VId wherein $R^{2a}$ and $Y^c$ are as defined above.

Finally a compound of formula VId is alkylated with a compound of the formula $$L\text{-}(CH_2)_n\text{—}NR^aR^b$$

in which L is a bromo or, preferably, a chloro moiety, and $R^{2a}$ and $Y^c$ optionally are dealkylated by standard procedures, to provide compounds of formulae VIe and VIf, respectively.

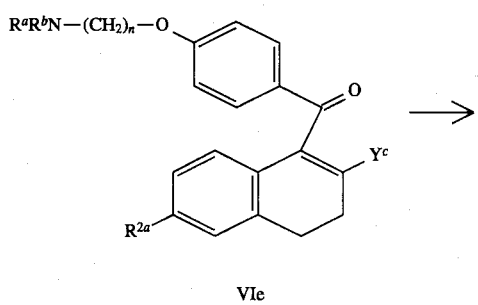

VIe

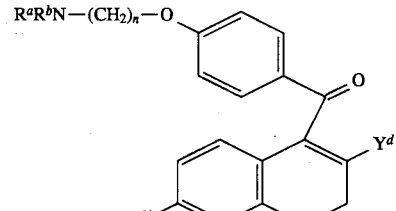

VIf wherein $R^{2b}$ is —H or —OH and $Y^d$ is phenyl, benzyl, hydroxyphenyl, or hydroxybenzyl.

In the process for preparing compounds of formula vie or VIf, it is evident that the particular sequence of synthetic steps designed to produce a compound having substituents of particular definition and location is such as one of ordinary skill in the art will recognize.

The compounds of Formula VIf can be substituted using standard means, if desired, to produce the corresponding dihydronaphthenyl compounds of Formula I.

B. Preparation of Naphthalenyl Compounds

Those compounds of Formula I which are substituted naphthalenes are readily prepared from the corresponding dihydronaphthalenyl compounds. Selective dehydrogenation of the dihydronaphthalene structure to produce specifically the corresponding naphthalene can be accomplished by treatment with 2,3-dichloro-5,6-dicyano- 1,4-benzoquinone (DDQ) at a temperature of from about 50° C. to about 100° C. The naphthalene which is produce may be further converted to other naphthalene compounds by means of the derivatizing reactions described supra.

EXAMPLE 1

Preparation of 3-(4-Methoxyphenyl)-4-[4-(2-pyrrolidin-1-ylethoxy)benzoyl-1,2-dihydronaphthalene, Citrate Salt The title compound was prepared as described in U.S. Pat. No. 4,230,862. To a suspension of sodium amide (15.2 g, 0.38 mol) in 250 ml of tertrahydrofuran were added 50 grams (0.34 mol) of β-tetralone. The mixture was stirred for 15–20 minutes, and 78 grams of phenyl p-methoxybenzoate dissolved in tetrahydrofuran were added. The temperature of the reaction mixture was maintained below 10° C., and the mixture was then stirred at room temperature overnight. The reaction mixture was concentrated and the water was added to the residue. The aqueous mixture was extracted with ethyl acetate, and the ethyl acetate extract was washed and concentrated.

The residue was chromatographed on silica using benzene as eluant. The purer fractions obtained by the chromatographic separation were combined and concentrated, and the residue was dissolved in a minimum of methanol. The methanol was cooled, and 35.2 grams of 1-(4-methoxybenzoyl)-2-tetralone were collected by filtration.

4-Bromoanisole (18.7 g, 0.1 mol) was added dropwise in ether to tetrahydrofuran containing 5 drops of 1,2-dibromoethane and 3.6 grams (0.15 mol) of magnesium. Reaction occurred almost immediately, and the addition was continued at a slow rate with evolution of heat sufficient to maintain a general reflux. Upon completion of the addition, the above substituted b-tetralone dissolved in acetone was added dropwise with stirring over a two hour period, the mixture being maintained at 40° C. The resulting mixture was then poured into cold, dilute hydrochloric acid, and the acidic mixture was extracted with ethyl acetate. The ethyl acetate extract was washed, dried, and concentrated to an oil. The oil was chromatographed over silica using benzene as eluant. A subsequent elution of the column with a mixture of benzene containing two percent ethyl acetate yielded 15 grams of 3-(4-methoxyphenyl)-4-(4-methoxybenzoyl)-1,2-dihydronaphthalene as an oil.

A mixture of 11.1 grams (0.03 mol) of the above dimethoxy product, 7.2 grams of sodium hydride (50 percent in oil), and 11 ml of ethyl mercaptan in N,N-dimethylformamide was prepared. The mixture was heated to 65°–70° C. and maintained at that temperature for about two hours. The mixture was then cooled and conetrated. The concentrate was acidified and extracted with ethyl acetate. The ethyl acetate extract was washed, dried, and evaporated. The residue was dissolved in benzene and chromatographed over silica to obtain five grams of an oil comprising relatively pure 3-(4-methoxyphenyl)-4-(4-hydroxybenzoyl)-1,2-dihydronaphthalene.

The above phenolic product (4.3 g, 0.01 mol) was dissolved in N,N-dimethylformamide. To this solution was added 0.7 grams of sodium hydride (50 percent in oil), and the resulting mixture was warmed to 40° C. for one hour and then was cooled to room temperature. To the mixture then were added 1.6 grams of 1-chloro-2-pyrrolidinoethane, and the mixture was warmed to 60° C. and maintained at this temperature for about two hours. The reaction mixture was then stirred at room temperature overnight.

The mixture was concentrated, and water was added to the residue. The aqueous mixture was extracted with ethyl acetate. The ethyl acetate extract was washed and concentrated to a residue. The residue was extracted with hexanes, the insoluble portion was dissolved in ethyl acetate, and the ethyl acetate solution was extracted with 1N hydrochloric acid. The acid extract was rendered alkaline, and then was extracted with ethyl acetate. The ethyl acetate extract was washed and concentrated. One equivalent of citric acid in acetone then was added to the concentrate, and the mixture was concentrated to dryness. The residue was dissolved in a large volume of methyl ethyl ketone. The ketone solution was concentrated to about 300 ml and was cooled to 0° C. The title product, the citrate salt of 3-(4-methoxyphenyl)-4-[4-(2-pyrrolidin-1-ylethoxy)benzoyl-1,2-dihydronaphthalene, was collected by filtration and vacuum dried. mp 82°–85° C.

Analysis for $C_{36}H_{39}NO_{10}$: Theory: C, 66.96; H, 6.09; N, 2.17; O, 24.78. Found: C, 66.70; H. 6.27; N, 2.27; O, 24.54.

EXAMPLE 2

Preparation of 3-Phenyl-4-[4-(2-pyrrolidin-1-ylethoxy)benzoyl]-7-methoxy-1,2-dihydronaphthalene The title product was prepared as described iin U.S. Pat. No. 4,230,862. To 300 ml of N,N-dimethylformamide were added 107 grams of phenyl p-hydroxybenzoate and 26 grams of sodium hydride (50 percent in oil). The mixture was heated to 60° C. and maintained at this temperature for about two hours. To this mixture was added 1-chloro-2-pyrrolidin-1-ylethane (67 g), and the mixture was stirred overnight at 85° C. The bulk of the N,N-dimethylformamide then was evaporated from the mixture. Water was added to the residue, and the aqueous mixture was extracted with ethyl acetate. The ethyl acetate extract was concentrated, and the residue was dissolved in a 1:1 mixture of ether and ethyl acetate. The organic solution was then extracted with 2N hydrochloric acid, and the acid extract was added dropwise to 2N sodium hydroxide. The resulting mixture was extracted with ethyl acetate, and the ethyl acetate extract was washed and then dried over magnesium sulfate. The ethyl acetate was concentrated to obtain 110 grams of crude phenyl p-(2-pyrrolidin-1-ylethoxy)benzoate.

To a suspension of 20 grams (0.5 mol) of sodium amide in tetrahydrofuran were added dropwise 41.7 grams of 6-methoxy-2-tetralone in tetrahydrofuran, the temperature of the mixture being maintained below 10° C. Upon completion of the addition, the mixture was stirred for 20 minutes, the reaction mixture being maintained below 10° C., after which time an exothermic reaction occurred, the reaction temperature rising to about 20° C.

The above prepared phenyl p-(2-pyrrolidin-1-ylethoxy)benzoate, dissolved in tetrahydrofuran, was then added dropwise, and the mixture was stirred overnight at room temperature. The mixture was poured into water, and the resulting mixture was extracted with ethyl acetate. The ethyl acetate extract was washed several times with water, and dried over magnesium sulfate. The ethyl acetate was concentated to obtain about 100 grams of crude material which was dissolved in 1.5 liters of acetone, and one equivalent of citric acid in 400 ml of ethyl acetate was added. The resulting solid was isolated by filtration and vacuum dried to obtain 85.9 grams of 6-methoxy-1-[4-(2-pyrrolidin-1-ylethoxy)benzoyl]-2-tetralone. The product was then chromatographed over silica using ethyl acetate as eluant, and the citrate salt was prepared from the recovered product.

The above product (8.6 g, 0.02 mol) was added to a solution of phenylmagnesium bromide in tetrahydrofuran. The resulting mixture was stirred for one hour at room temperature and then was warmed to 50° C. and maintained at this temperature for three hours. The resulting mixture was poured into a mixture of ice and hydrochloric acid, and the acid mixture was extracted with ethyl acetate. The ethyl acetate extract was washed, dried, and concentrated to obtain 10.5 grams of a red-brown oil. The oil was added to 500 ml of acetic acid, and the mixture was heated on a steam bath for about 30 minutes. The acid was stripped off, and water as added to the residue.

The aqueous mixture was rendered alkaline by addition of base, and the alkaline mixture was extracted with ethyl acetate. The extract was dried and concentrated to obtain 8.7 grams of product which was dissolved in acetone, and one equivalent of citric acid was added to the mixture. The acetone was stripped off, and methyl ethyl ketone was added to the residue. The mixture was maintained at 0° C. overnight, and the crystals which formed were collected by filtration and washed with cold methyl ethyl ketone and vacuum dried. The solid was recrystallized from acetone to obtain the title compound in the form of its citrate salt. mp 98°–100° C.

Analysis of $C_{36}H_{39}NO_{10}$: Theory: C, 66.96; H, 6.09; N, 2.17; O, 24.78. Found: C, 66.72; H, 6.27; N, 2.09; O, 24.50.

The title compound in the form of its free base was generated by treatment of the citrate salt with dilute alkali.

Analysis for $C_{30}H_{31}NO_5$: Theory: C, 79.44; H, 6.89; N, 3.09. Found: C, 79.19; H, 6.68; N, 2.91.

EXAMPLE 3

Preparation of
3-Phenyl-4-[4-(2-pyrrolidin-1-ylethoxy)benzoyl]
-1,2-dihydronaphthalene The title product was prepared as described in U.S. Pat. No. 4,230,862. To a solution of 5.0 grams (18 mmol) of 1-(4-methoxybenzoyl)-2-tetralone (prepared as described in Example 1) in 50 ml of ether was added dropwise at 0° C. a solution of phenylmagnesium bromide (18 mmol) in 9 ml of ether. Upon completion of the addition, the mixture was stirred for twenty minutes. Thin layer chromatography of the reaction mixture indicated the presence of starting material. An additional 13.5 ml of the phenylmagnesium bromide solution were added.

The mixture was refluxed for two hours and then was cooled and poured over iced aqueous ammonium chloride solution. The organic layer was separated and washed with brine. The mixture was then dried over magnesium sulfate, filtered, and evaporated to give about ten grams of a yellow oil. After a wash with hexanes, the product was further purified by chromatography to give 4.67 grams of 3-phenyl-4-(4-methoxybenzoyl)-1,2-dihydronaphthalene.

To 2.0 grams (6 mmol) of the above dihydronaphthalene, dissolved in 10 ml of N,N-dimethylformamide, were added sodium thioethoxide (7.5 mmol), dissolved in 15 ml of N,N-dimethylformamide. The addition was carried out under a nitrogen atmosphere and at 80° C. The mixture was maintained at 80° C. for fifteen hours. The mixture was then cooled and poured into an iced aqueous ammonium chloride solution. The resulting mixture was extracted with ethyl acetate, and the ethyl acetate extract was washed four times with brine.

The ethyl acetate extract was dried over magnesium sulfate an evaporated to give an oil which was further purified by chromatography on a silica column, suing benzene toelute impurities. The product was then eluted with ethyl acetate to give, upon evaporation of the ethyl acetate, 1.69 grams of 3-phenyl-4-(4-hydroxybenzoyl)- 1,2-dihydronaphthalene as a clear pale yellow oil.

A mixture of 1.61 grams (4.95 mmol) of the above product in 10 ml of dry N,N-dimethylformamide containing 119 mg (4.95 mmol) of sodium hydride and freshly distilled 1-chloro-(2-pyrrolidin-1-yl)ethane. The addition was made under a nitrogen atmosphere with the temperature being maintained at about 10° C. Upon completion of the resulting efferverscence, the mixture was heated to 80° C. and maintained at that temperature for about two hours. The mixture was then poured into water, and the total was extract with ether. The ether extract was washed five times with brine, and dried over magnesium sulfate. The ether layer was then filtered and evaporated to give a gray oil, which was further purified by chromatography to give 3-phenyl-4-[4-(2-pyrrolidin-1-ylethoxy)benzoyl]1,2-dihydronaphthalene.

The product was converted to the corresponding citrate salt by treatment with 0.59 grams of citric acid in 50 ml of hot acetone. The resulting mixture was evaporated to dryness, and the residue was stirred for about fifteen hours with ether to obtain the citrate salt. mp 89°–93° C.

Analysis for $C_{33}H_{37}NO_9.0.5\ H_2O$: Theory: C, 67.34; H, 6.13; N, 2.25. Found: C, 67.06; H, 6.41; N, 2.66.

EXAMPLE 4

Preparation of
1-[4-(2-Pyrolidin-1-ylethoxy)benzoyl]-2-
phenylnaphthalene, Citrate Salt The title product was prepared as described in U.S. Pat. No. 4,230,862. To 30 ml of dioxane were added 3-phenyl-4-(4-methoxybenzoyl)-1,2-dihydronaphthalene (1.90 g, 5.58 mmol), prepared as described in Example 3, supra, and 2,3-dichloro-5,6-dicyano-1,4-benzoquinone (2.00 g, 8.81 mmol). The resulting mixture was heated to reflux and refluxed for twelve hours under a nitrogen atmosphere. The mixture was then cooled and evaporated to dryness. The residue was partitioned between ether and water. The organic fraction was washed 5N sodium hydroxide (5×20 ml), followed by a wash with brine. The mixture was then dried over magnesium sulfate and evaporated to give 1.9 grams of substantially pure 1-(4-methoxybenzoyl)-2-phenylnaphthalene.

Employing substantially the same demethylation procedure as described in Example 3, 1.83 grams (5.41 mmol) of the above product were treated with sodium thioethoxide to obtain 1.4 grams of 1-(4-hydroxybenzoyl)-2-phenylnaphthalene.

To 10 ml of N,N-dimethylformamide were added 1.25 grams of the above product. The resulting mixture was added at about 10° C. to a mixture of 20 ml of N,N-dimethylformamide containing 120 mg (5.0 mmol) of sodium hydride and 800 mg of 1-chloro-2-(pyrrolidin-1-yl)ethane. Upon completion of the resulting effervescence, the mixture was heated to 80° C. and maintained at that temperature for about three hours, during which time sodium chloride precipitated. The mixture was cooled and evaporated to dryness. The resulting residue was partitioned between water and ethyl acetate. The organic fraction was washed with brine (5×25 ml). The organic fraction was dried and evaporated to give 1.62 grams of 1-[4-[2-(pyrrolidin-1-yl)ethoxy] benzoyl]-2-phenylnaphthalene as a yellow oil.

The above free base was converted to the corresponding citrate salt in accordance with the method of Example 3, employing 0.811 grams of citric acid hydrate. The title compound was obtained as an amorphous solid which crystallized on standing overnight in ether. mp 105°–108° C. Analysis for $C_{33}H_{35}NO_9 \cdot H_2O$: Theory: C, 65.55; H, 5.90; N, 2.22. Found: C, 66.90; H, 5.85; N, 2.25.

EXAMPLE 5

Preparation of
3-(4-Methoxyphenyl)-4-[4-[2-(piperidin-1-yl)ethoxy]benzoyl]-1,2-dihydronaphthalene, Citrate Salt The title compound was prepared as described in U.S. Pat. No. 4,230,862. To a suspension of sodium hydride (0.269 g, 11 mmol), washed free of mineral oil, and 1-chloro-2-(piperidin-1-yl)ethane (1.82 g, 12 mmol) in N,N-dimethylformamide (50 ml) at 0° C., and under a nitrogen atmosphere, were added 4.0 grams (10 mmol) of 3-(4-methoxyphenyl)-4-(4-hydroxybenzoyl)-1,2-dihydronaphthalene, prepared as described in Example 1, dissolved in 20 ml of N,N-dimethylformamide. The solution was added dropwise with stirring. When the effervescence had ceased for the most part, the mixture was heated to 50° C. and maintained at that temperature for several hours. The progress of the reaction was monitored by thin layer chromatography.

Once the reaction had progressed sufficiently, the N,N-dimethylformamide was evaporated, and the concentrated mixture was poured over ice water and ethyl acetate. The ethyl acetate fraction was washed with brine, dried over potassium carbonate, filtered, and evaporated, The resulting oil was chromatographed over a 1.5"×12" silica column using the following as a double gradient:

(i) 10 percent ethyl acetate in benzene (500 ml)→20 percent ethyl acetate in benzene (2 liters);

(ii) 20 percent ethyl acetate in benzene (1.5 liters)→1:1 mixture of methanol and ethyl acetate (1.5 liters).

The appropriate fractions were concentrated to give an almost colorless oil. The oil was dissolved in ethyl acetate, and the ethyl acetate solution was dried over potassium carbonate, filtered, and evaporated to give 4.7 grams of the free base of the title compound as a pale yellow oil.

The free base (3.4 g, 7.28 mmol) was treated with citric acid monohydrate (1.49 g, 7.1 mmol) in about 20 ml of boiling acetone. When a clear solution was obtained, the acetone was evaporated, 300 ml of anhydrous ether was added, and the resulting precipitate was stirred overnight. The title compound (5.2 grams) was collected as a white powder.

Analysis for $C_{37}H_{41}NO_{10}$: Theory: C, 67.36; H, 6.26; N, 2.12. Found: C, 67.25; H, 5.96; N, 1.84.

EXAMPLE 6

Preparation of
3-(4-Methoxyphenyl)-4-[4-(2-dimethylaminoethoxy)-benzoyl]-1,2-dihydronaphthalene, Citrate Salt The title compound was prepared as described in U.S. Pat. No. 4,230,862. To 50 ml of acetone were added 4.0 grams (11.2 mmol) of 3-(4-methoxyphenyl)-4-(4-hydroxybenzoyl)-1,2-dihydronaphthalene, prepared as described in Example 1, 1.81 grams (16.8 mmol) of 1-chloro-2-dimethylaminoethane (freshly prepared from the hydrohloride), and 2.32 grams (16.8 mol) of finely powdered potassium chloride. The resulting mixture was refluxed under nitrogen with stirring for about 72 hours. The progress of the reaction was monitored by thin layer chromatography.

The resulting mixture was then poured over ice, and the resulting mixture was extracted with ether. The ether was washed three times with brine, dried over potassium carbonate, filtered, and evaporated to obtain 4.51 grams of the free base of the title compound as a brown oil.

The oil was vacuum dried and then was converted to the citrate salt by treatment with 2.17 grams (10.4 mmol) of citric acid monohydrate in 50 ml of hot acetone. Evaporation of the acetone and stirring of the residue with ether gave 5.2 grams of the title compound as an amorphous solid.

Analysis for $C_{34}H_{37}NO_{10}$: Theory: C, 65.90; H, 6.02; N, 2.26. Found: C, 66.17; H, 6.23; N, 2.37.

EXAMPLE 7

Preparation of
3-(4-Hydroxyphenyl)-4-[4-[2-(pyrrolidin-1yl)ethoxy]benzoyl]-1,2-dihydronaphthalene, Mesylate Salt The title compound was prepared as described in U.S. Pat. No. 4,230,862. To 25 ml of methyl ethyl ketone were 10 grams (2.92 mmol) of 3-(4-hydroxyphenyl)-4-( 4-hydroxybenzoyl)-1,2-dihydronaphthalene, 0.497 grams (2.92 mmol) of 1-chloro-2-(pyrrolidin-1-yl)ethane, and 1.21 grams (8.77 mmol) offinely powdered potassium carbonate. The resulting mixture was refluxed for 16 hours. The mixture was then cooled and poured into a mixture of water and ethyl acetate. The resulting mixture was rendered acidic by addition of 1N hydrochloric acid and then alkaline by the addition of sodium bicarbonate.

The organic fraction was washed with brine, dried over magnesium sulfate, and evaporated to give a yellow oil. The resulting oil was further purified by chromatography. The free base (362 mg, 0.825 mmol) as converted to the mesylate aslt by treatment with an equivalent of methanesulfonic acid in acetone to yield the title compound as an amorphous solid.

Analysis for $C_{31}H_{37}NO_6S$: Theory: C, 67.27; H, 6.21; N, 2.61. Found: C, 67.25; H, 6.19; N, 2.69.

EXAMPLE 8

Preparation of 3-(4-Methoxyphenyl)-4-[4-[2-(hexamethyleneimin-1-yl)benzoyl]-1,2-dihydronaphthalene, Mesylate Salt The title compound was prepared as described in U.S. Pat. No. 4,230,826. To 50 ml of methyl ethyl ketone were added 3.0 g (8.43 mmol) of 3-(4-methoxyphenyl)- 4-(4-hydroxybenzoyl)-1,2-dihydronaphthalene, 1.84 g (9.27 mmol) of 1-chloro-2-(hexamethyleneimin-1-yl)ethane hydrochloride, and 3.25 grams (25.3 mmol) of finely powdered potassium carbonate. The mixture was refluxed for 48 hours.

The mixture was then poured into water, and ethyl acetate was added. The resulting organic layer was separated, washed with brine, dried, and evaporated to a yellow oil. The oil was further purified by chromatography. The free base of the title compound was recovered (2.51 g) as a pale yellow oil. The oil was treated with 0.431 g (4.48 mmol) of methanesulfonic acid in 10 ml of acetone. Upon scratching and cooling of the mixture, crystals formed. The mixture was cooled overnight and 1.97 grams of the title compound were obtained as a white crystals. mp 123°–125° C.

Analysis for $C_{34}H_{41}NO_6S$: Theory: C, 68.61; H, 6.80; N, 2.42. Found: C, 68.38; H, 6.62; N, 2.40.

EXAMPLE 9

Preparation of 3-(4-Methoxyphenyl)-4-[4-[2-(piperidin-1-yl)ethoxy]benzoyl]-1,2-dihydronaphthalene, Mesylate Salt The title compound was prepared as described in U.S. Pat. No. 4,230,862. To 150 ml of methyl ethyl ketone were added 7.8 g (21.9 mmol) of 3-(4-methoxyphenyl)- 4-(4-hydroxybenzoyl)-1,2-dihydronaphthalene, 4.84 grams (23.6 mmol) of 1-chloro-2-(piperidin-1-yl)ethane hydrochloride, and 14.5 grams (109 mmol) of potassium carbonate. The resulting mixture was refluxed overnight.

The mixture was then poured into a mixture of water and ethyl acetate. The resulting orgnaic fraction was spearated, washed with brine, dried over magnesium sulfate, and evaporated in vacuo to obtain the free base of the title compound as a yellow oil.

The oil was dissolved in 30 ml of acetone and was treated with 2.105 grams (21.9 mmol) of methanesulfonic acid. The mixture was cooled and scratched, and the title compound was collected at –40° C. and ashed well with acetone and ether cooled to about –60° C. The solid was then vacuum dried at 100° C. to obtain 11.21 grams of the title compound as a white crystalline solid. mp 157°–158° C.

Analysis for $C_{33}H_{39}NO_6S$: Theory: C, 68.18; H, 6.62; N, 2.48. Found: C, 68.11; H, 6.76; N, 2.50.

EXAMPLE 10

Preparation of 3-(4-Methoxyphenyl)-4-(4-diethylaminoethoxybenzoyl)-1,2-dihydronaphthalene, Mesylate Salt To 75 ml of methyl ethyl ketone were added 4.0 grams (11.2 mmol) of 3-(4-methoxyphenyl)-4-(4 -hydroxybenzoyl)-1,2-dihydronaphthalene, 2.41 grams (14 mmol) of 1-chloro-2-diethylaminoethane hydrochloride, and 7.93 grams (56 mmol) of finely powdered potassium carbonate. The mixture was refluxed overnight, and, employing the method of Example 9, 5.67 grams of the free base of the title compound were obtained as a yellow oily material.

The oil was treated with 1.07 grams (11.2 mmol) of methanesulfonic acid in about 15 ml of acetone. The resulting mixture was maintained with cooling for several days after which white crystals appeared. The crystals were somewhat hygroscopic and were collected as quickly as possible and vacuum-dried. There were obtained 4.3 grams of the title compound as a white crystalline solid.

Analysis for $C_{31}H_{39}NO_6S$: Theory: C, 67.24; H, 7.10; N, 2.53. Found: C, 67.48; H, 6.92; N, 2.43.

EXAMPLE 11

Preparation of 3-(4-Methoxyphenyl)-4-(4-diisopropylaminoethoxybenzoyl)-1,2-dihydronaphthalene, Mesylate Salt To 75 ml of methyl ethyl ketone were added 3.84 grams (10.8 mmol) of 3-(4-methoxyphenyl)-4-(4 -hydroxybenzoyl)-1,2-dihydronaphthalene, 2.70 grams (13.5 mmol) of 1-chloro-2-diisopropylaminoethane hydrochloride, and 7.11 grams (54 mmol) of finely powdered potassium carbonate. The mixture was allowed to reflux overnight, and, upon workup, in accordance with the procedure of Example 9, 5.64 grams of the free base of the title compound were obtained as a yellow oily substance. The oily product was treated with 1.04 grams (10.8 mmol) of methanesulfonic acid in about 25 ml of acetone. The mixture was cooled, and crystals slowly appeared. The crystals collected at –40° C. with the aid of acetone cooled to –60° C. Vacuum drying of the product gave 5.1 grams.

Analysis for $C_{33}H_{41}NO_6S$: Theory: C, 68.37; H, 7.31; N, 2.42. Found: C, 68.08; H, 6.91; N, 2.21.

The following compounds were prepared essentially as described in the above examples:

EXAMPLE 12

3-Hydroxy-4-[4-[2-(pyrrolidin-1-yl)ethoxy]-benzoyl]-1,2-dihydronaphthalene, Sodium Salt

EXAMPLE 13

2-(4-Methoxyphenyl)-1-[4-[2-(pyrrolidin-1-yl)ethoxy]benzoyl]naphthalene, Mesylate Salt

EXAMPLE 14

3-(4-Methoxyphenyl)-4-[4-[2-(piperidin-1-yl)ethoxy]benzoyl]-7-methoxy-1,2-dihydronaphthalene, Mesylate Salt

EXAMPLE 15

3-(4-Methoxyphenyl)-4-[4-(2-dimethylaminoethoxy)-benzoyl]- 1,2-dihydronaphthalene, 2-Hydroxy-1,2,3-propanetricarboxylic Acid Salt

EXAMPLE 16

3-(4-Methoxyphenyl)-4-[4-[2-(N-methyl-1-pyrrolidinium)ethoxy]benzoyl]-1,2-dihydronaphthalene, Iodide Salt

EXAMPLE 17

3-(4-Methoxyphenyl)-4-[4-[2-(pyrrolidin-1-yl)ethoxy]benzoyl]-1,2-dihydronaphthalene, Mesylate Salt The biological activity of the compounds of the present invention was evaluated employing an initial screening assay which rapidly and accurately measured the binding of the tested compound to known bradykinin receptor sites. Assays useful for evaluating bradykinin receptor antagonists are well known in the art. See, e.g., U.S. Pat. Nos. 5,162,497, issued Nov. 10, 1992; 5,212,182, issued May 18, 1993; 5,216,165, issued Jun. 1, 1993; and 5,288,725, issued Feb. 22, 1994, all of which are herein incorporated by reference. See also, Ransom, et al., *Biochemical Pharmacology*, 43:1823 (1992).

Guinea Pig Bradykinin Binding Assay

Guinea pigs were humanely sacrificed and the intestines were removed. These intestines were washed thoroughly with 0.9% saline, blotted dry and weighed. The tissues were homogenized in at least four volumes of 50 mM Tris buffer, pH 7.7, and centifuged at 15,000 g for about thirty minutes.

The pellets were then washed three times by successive suspensions in 50 mM Tris, pH 7.7, followed by centifugation. The final pellets were resuspended in a sufficient volume of 50 mM Tris, pH 7.7 to provide a concentration of 1 g of wet weight of tissue per 4 ml of buffer. These samples were stored frozen at −80° C.

For the binding assay 190–195 µl of assay buffer [50 mM Tris, pH 7.4, 1 mM 1,10-phenanthroline, and 10 µM Plummer's inhibitor] was admixed with 200 µl of tissue homogenate, and 5–10 µl of test sample, the additions occurring in the order listed. This assay mixture was then mixed throughly. Non-specific binding was determined in the presence of 1 µM unlabeled bradykinin.

To this assay cocktail was added 100 µl (1 nM) $^3$H-labeled bradykinin. The binding reaction was then incubated for about 90 minutes at room temperature and then filtered through GF/B glass fiber filters, the filters having been presoaked for at least one hour in 0.3% polyethyleneimine. The filters were washed with cold 50 mM Tris, pH 7.7 (3×3 ml) and then counted on a scintillation counter.

Many of the compounds prepared supra showed significant activity as bradykinin receptor antagonists. As the compounds of Formula I are effective bradykinin receptor antagonists, these compounds are of value in the treatment of a wide variety of clinical conditions which are characterized by the presence of an excess of bradykinin. Thus, the invention provides methods for the treatment or prevention of a physiological disorder associated with an excess of bradykinins, which method comprises administering to a mammal in need of said treatment an effective amount of a compound of Formula I or a pharmaceutically acceptable salt, solvate or prodrug thereof. The term "physiological disorder associated with an excess of bradykinins" encompasses those disorders associated with an inappropriate stimulation of bradykinin receptors, regardless of the actual amount of bradykinin present in the locale.

These physiological disorders may include disorders such as rhinitis, asthma, irritable bowel syndrome, ulcerative colitis, pain or nociception, inflammation, periodontitis, rheumatoid arthritis,and osteomyelitis. Bradykinins are also known to have important roles in circulation homeostasis and bradykinin receptor antagonists may, therefore, be useful in blood pressure regulation and the treatment or prevention of hypertension or hypotension. Bradykinin receptor antagonists are also useful in the treatment or prevention of endotoxic shock which results from an interaction of endotoxin produced from bacterial cell walls with cells of the reticuloendothelial system.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention employs pharmaceutical compositions which contain, as the active ingredient, the compounds of Formula I associated with pharmaceutically acceptable carriers. In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

Capsules, each containing 15 mg of medicament, are made as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

FORMULATION EXAMPLE 9

An intravenous formulation may be prepared as follows:

| Ingredient | Quantity |
| --- | --- |
| Active Ingredient | 250.0 mg |
| Isotonic saline | 1000 ml |

FORMULATION EXAMPLE 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

FORMULATION EXAMPLE 11

Sublingual or buccal tablets, each containing 10 mg of active ingredient, may be prepared as follows:

| Ingredient | Quantity Per Tablet |
| --- | --- |
| Active Ingredient | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by refernce.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A method for the treatment or prevention of a physiological disorder associated with an excess of bradykinins in which a bradykinin receptor is inhibited, which method comprises administering to a mammal in need of said treatment an effective amount of a compound of the formula

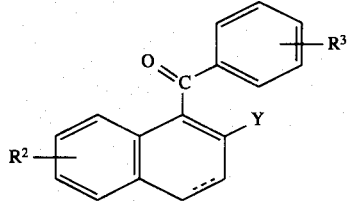

wherein:

$R^2$ is hydrogen, hydroxy, or $C_1$–$C_6$ alkoxy;

the dotted line represents an optional covalent bond;

Y is hydroxy, or

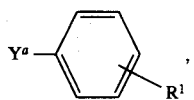

where $Y^a$ is a bond, —$CH_2$, or —$CH_2CH_2$—; and $R^1$ is hydrogen, $C_1$–$C_6$ alkyl, $C_1$–$C_6$ alkoxy, or hydroxy;

$R^3$ is aryloxy, $C_1$–$C_6$ alkoxy, hydroxy or

-Q-$(CH_2)_n$—$NR^aR^b$ where,

Q is —O— or —$CH_2$, n is 1–6, $R^a$ and $R^b$ are independently hydrogen or $C_1$–$C_6$ alkyl or are taken together with the nitrogen to which they are bonded to constitute a heterocyclic ring selected from the group consisting of pyrrolidinyl, piperazinyl, piperidinyl, hexamethyleneiminyl, 4-methylpiperidinyl, imidazolinyl, heptamethyleneiminyl, morpholinyl, and N-methylpyrrolidinyl;

or a pharmaceutically acceptable salt or solvate thereof.

2. A method as claimed in claim 1 employing a compound wherein the optional double bond is absent, or a pharmaceutically acceptable salt or solvate thereof.

3. A method as claimed in claim 2 employing a compound wherein Y is

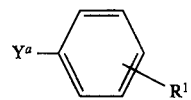

or a pharmaceutically acceptable salt or solvate thereof.

4. A method as claimed in claim 3 employing a compound wherein $Y^a$ is a bond or —$CH_2$— or a pharmaceutically acceptable salt or solvate thereof.

5. A method as claimed in claim 4 employing a compound wherein $R^1$ is hydrogen, hydroxy, methyl, ethyl, methoxy, or ethoxy, or a pharmaceutically acceptable salt or solvate thereof.

6. A method as claimed in claim 5 employing a compound wherein $R^3$ is -Q-$(CH_2)_n$—$NR^aR^b$, or a pharmaceutically acceptable salt or solvate thereof.

7. A method as claimed in claim 6 employing a compound wherein Q is —O—, or a pharmaceutically acceptable salt or solvate thereof.

8. A method as claimed in claim 6 employing a compound wherein n is 1, 2, or 3, or a pharmaceutically acceptable salt or solvate thereof.

9. A method as claimed in claim 8 employing a compound wherein $NR^aR^b$ is pyrrolidinyl, piperazinyl, piperidinyl, hexamethyleneiminyl, imidazolinyl, heptamethyleneiminyl, morpholinyl, or N-methylpyrrolidinyl, or a pharmaceutically acceptable salt or solvate thereof.

10. A method as claimed in claim 9 employing a compound selected from the group consisting of 3-(4-methoxyphenyl)- 4-[4-(2-pyrrolidin-1-ylethoxy)benzoyl-1,2-dihydronaphthalene, 3-phenyl-4-[4-(2-pyrrolidin-1-ylethoxy)benzoyl] -7-methoxy-1,2-dihydronaphthalene, 3-(4-methoxyphenyl)- 4-[4-[2-(piperidin-1-yl)ethoxy]benzoyl]-1,2-dihydronaphthalene, 3-(4-hydroxyphenyl)-4-[4-[2 -(pyrrolidin-1-yl)ethoxy]benzoyl]-1,2-dihydronaphthalene, 3 -(4-methoxyphenyl)-4-[4-[2-(hexamethyleneimin-1-yl)benzoyl] -1,2-dihydronaphthalene, 3-(4-methoxyphenyl)-4-[4-[2 -(piperidin-1-yl)ethoxy]benzoyl]-1,2-dihydronaphthalene, 3 -(4-methoxyphenyl)-4-[4-[2-(piperidin-1-yl)ethoxy]benzoyl] -7-methoxy-1,2-dihydronaphthalene, and 3-(4-methoxyphenyl)- 4-[4-[2-(N-methyl-1-pyrrolidinium)ethoxy]benzoyl]-1,2-dihydronaphthalene, or a pharmaceutically acceptable salt or solvate thereof.

11. A method as claimed in claim 8 employing a compound wherein $NR^aR^b$ is di($C_1$–$C_6$ alkyl)amino, or a pharmaceutically acceptable salt or solvate thereof.

12. A method as claimed in claim 11 employing a compound selected from the group consisting of 3-(4 -methoxyphenyl)-4-[4-(2-dimethylaminoethoxy)benzoyl]-1,2-dihydronaphthalene, 3-(4-methoxyphenyl)-4-(4 -diethylaminoethoxybenzoyl)-1,2-dihydronaphthalene, and 3-( 4-methoxyphenyl)-4-(4-diisopropylaminoethoxybenzoyl)-1,2-dihydronaphthalene, or a pharmaceutically acceptable salt or solvate thereof.

13. A method as claimed in claim 1 wherein the condition associated with an excess of bradykinin is pain or nociception.

14. A method as claimed in claim 1 wherein the condition associated with an excess of bradykinin is inflammation.

15. A method as claimed in claim 1 wherein the physiological disorder associated with an excess of bradykinin is rhinitis.

16. A method as claimed in claim 1 wherein the physiological disorder associated with an excess of bradykinin is asthma.

17. A method as claimed in claim 1 wherein the physiological disorder associated with an excess of bradykinins is hypertension.

18. A method as claimed in claim 1 wherein the physiological disorder associated with an excess of bradykinins is endotoxic shock.

\* \* \* \* \*